United States Patent [19]
Joseph

[11] Patent Number: 5,582,167
[45] Date of Patent: Dec. 10, 1996

[54] METHODS AND APPARATUS FOR REDUCING TRACHEAL INFECTION USING SUBGLOTTIC IRRIGATION, DRAINAGE AND SERVOREGULATION OF ENDOTRACHEAL TUBE CUFF PRESSURE

[75] Inventor: Jeffrey I. Joseph, Penn Valley, Pa.

[73] Assignee: Thomas Jefferson University, Philadelphia, Pa.

[21] Appl. No.: 204,481

[22] Filed: Mar. 2, 1994

[51] Int. Cl.$^6$ ............................................. A61M 15/00
[52] U.S. Cl. ................................ 128/207.15; 128/202.22
[58] Field of Search .................. 128/202.22, 207.15, 128/207.14, 205.23

[56] References Cited

U.S. PATENT DOCUMENTS

| | | | |
|---|---|---|---|
| 2,854,982 | 10/1958 | Pagano | 128/348 |
| 3,593,713 | 7/1971 | Bogoff | 128/246 |
| 4,305,392 | 12/1981 | Chester | 128/207.15 |
| 4,327,721 | 5/1982 | Goldin et al. | 128/207.15 |
| 4,334,534 | 6/1982 | Ozaki | 128/207.15 |
| 4,468,216 | 8/1984 | Muto | 604/43 |
| 4,584,998 | 4/1986 | McGrail | 128/207.15 |
| 4,607,635 | 8/1986 | Heyden | 128/207.15 |
| 4,632,108 | 12/1986 | Geil | 128/207.15 |
| 4,637,389 | 1/1987 | Heyden | 128/207.15 |
| 4,693,243 | 9/1987 | Buras | 128/207.15 |
| 4,762,125 | 8/1988 | Leiman et al. | 128/207.15 |
| 4,770,170 | 9/1988 | Sato et al. | 128/207.15 |
| 4,825,862 | 5/1989 | Sato et al. | 128/207.15 |
| 4,924,862 | 5/1990 | Levinson | 128/207.16 |
| 4,955,375 | 9/1990 | Martinez | 128/207.15 |
| 4,976,261 | 12/1990 | Gluck et al. | 128/207.15 |
| 4,977,894 | 12/1990 | Davies | 128/207.15 |
| 5,067,497 | 11/1991 | Greear et al. | 128/207.15 |
| 5,143,062 | 9/1992 | Peckham | 128/207.15 |
| 5,146,916 | 9/1992 | Catalani | 128/207.15 |
| 5,235,973 | 8/1993 | Levinson | 128/207.15 |
| 5,311,864 | 5/1994 | Huerta | 128/207.15 |
| 5,361,753 | 11/1994 | Pothmann et al. | 128/202.22 |
| 5,372,131 | 12/1994 | Heinen, Jr. | 128/207.15 |

OTHER PUBLICATIONS

Morris, et al., "An Electropneumatic Instrument For Measuring And Controlling The Pressures In The Cuffs Of Tracheal Tubes: 'The Cardiff Cuff Controller'," *J. Med. Eng. & Tech.*, vol. 9, No. 5 (Sep./Oct. 1985), pp. 229–230.

Cobley, et al., "Endobronchial Cuff Pressures," *British J. Anesthesia*, 70:576–78 (1993).

Willis, et al., "Tracheal Tube Cuff Pressure: Clinical Use Of The Cardiff Cuff Controller," *Anaesthesia*, 43:312–14 (1988).

(List continued on next page.)

*Primary Examiner*—Aaron J. Lewis
*Attorney, Agent, or Firm*—Woodcock Washburn Kurtz Mackiewicz & Norris

[57] ABSTRACT

An integrated system providing a mechanical and chemical barrier against the spread of infected secretions into the distal trachea is disclosed. An endotracheal tube used for patient airway management and provides a means to conveniently irrigate and drain the subglottic region below the vocal cords and above an inflated cuff. The subglottic region accumulates liquid secretions that may channel past an inflated endotracheal tube cuff, providing the necessary bacterial inoculum leading to bronchitis and nosocomial pneumonia. An irrigation channel delivers liquids such as saline or antibiotic and antifungal medications for mucosal hydration, and bactericidal action against infected subglottic secretions. An outer sleeve surrounding the endotracheal tube forms a suction lumen for removing the secretions. The tapered and compliant nature of this sleeve at body temperature allows a large suction channel without the need to greatly enlarge the outside diameter of the endotracheal tube at the vocal cord level. Electronic and mechanical controls provide regulated volume infusion and regulated suction. In addition, cuff pressure is servoregulated to the lowest pressure that provides a tracheal seal and rapid adjustment of cuff pressure so that peak airway pressures are attenuated, thus preserving mucosal perfusion. Pneumonia and patient mortality are thus prevented.

3 Claims, 1 Drawing Sheet

OTHER PUBLICATIONS

Spray, et al., "Aspiration Pneumonia: Incidence of Aspiration with Endotracheal Tubes," *Am. J. Surg.*, 131:701–03 (Jun. 1976).

Mahul, et al., "Prevention of nosocomial pneumonia in intubated patients: respective role of mechanical subglottic secretions drainage and stress ulcer prophylaxis," *Intensive Care Med.*, 18:20–25 (1992).

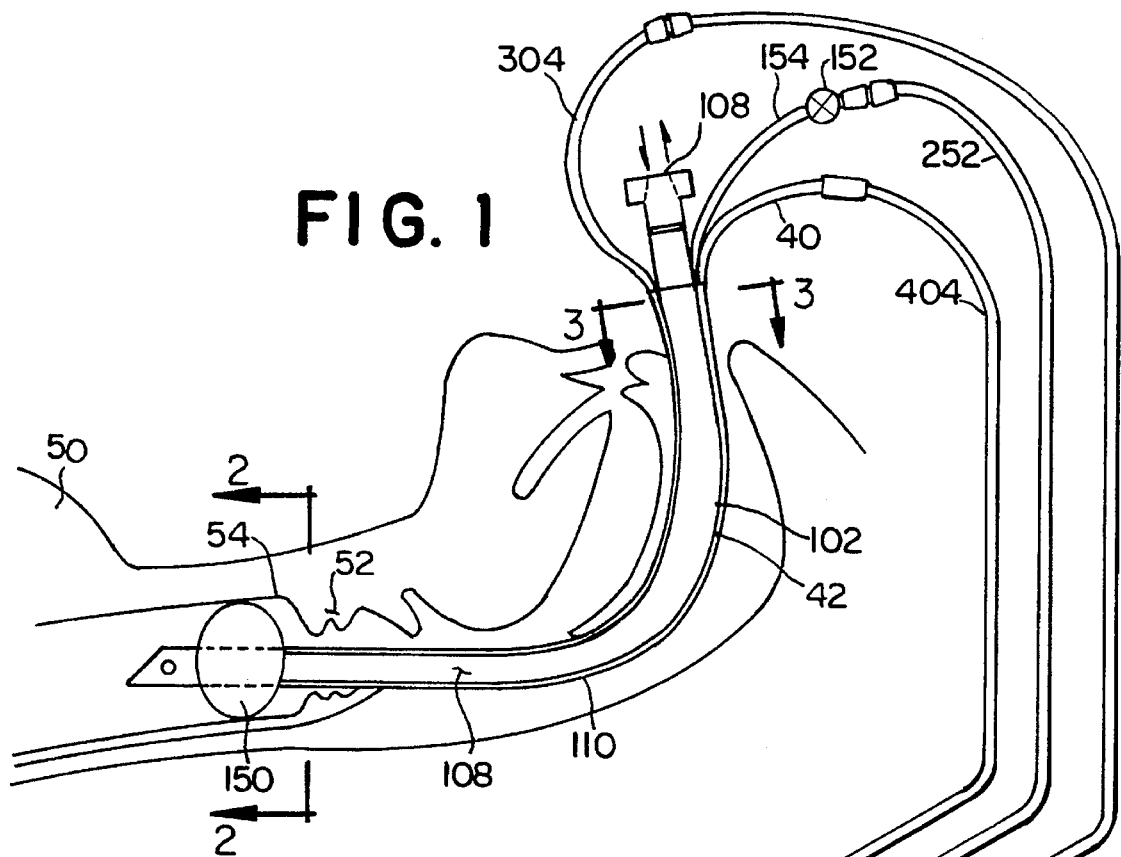
FIG. 1
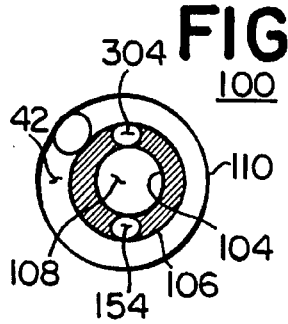
FIG. 3
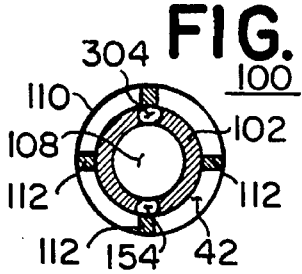
FIG. 2
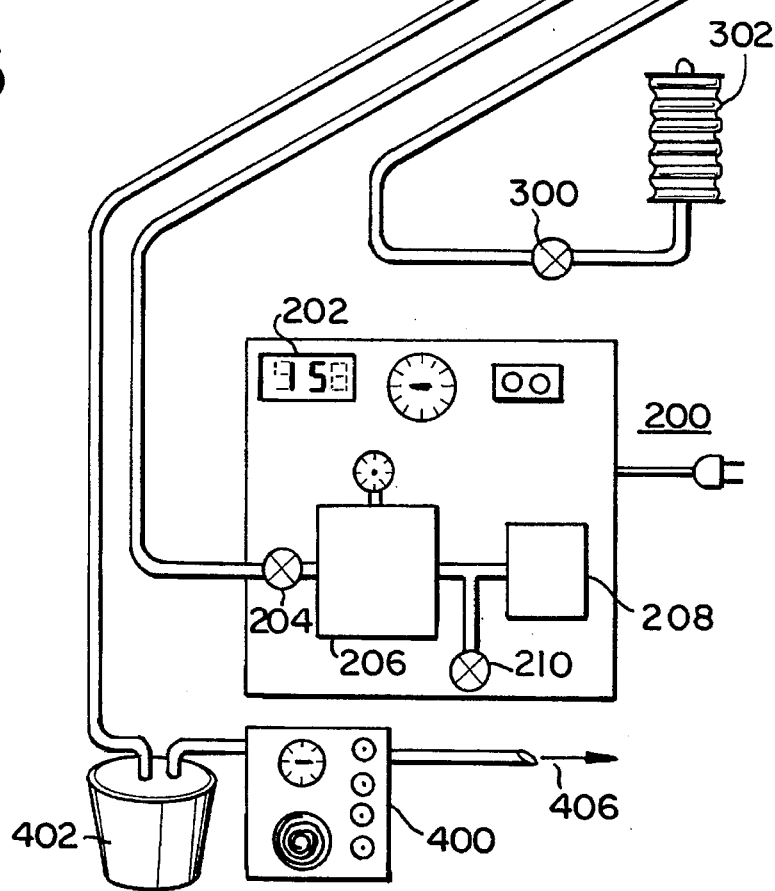

METHODS AND APPARATUS FOR REDUCING TRACHEAL INFECTION USING SUBGLOTTIC IRRIGATION, DRAINAGE AND SERVOREGULATION OF ENDOTRACHEAL TUBE CUFF PRESSURE

The present invention relates to tracheal tubes, and more specifically, relates to methods and apparatus for controlling the conditions of the intubation.

BACKGROUND OF THE INVENTION

Tracheal intubation is used in respiratory medicine to deliver or remove a fluid to the airways of a patient. Tracheal intubation with an endotracheal tube is commonly used during general anesthesia and when critically ill patients require airway protection and mechanical ventilation. Tracheal tubes include those used in tracheostomies as well as endotracheal tubes. Under certain conditions of long term ventilation, a tracheostomy tube is inserted through a surgical opening through the neck. An endotracheal tube is inserted into the trachea through either the mouth or nose (nasotracheal tube). Tracheal tubes are used for ventilation, and removal of secretions. Typically, endotracheal tubes are disposable plastic tubes, easily placed through the mouth or nose, that guarantee a patent conduit for the delivery of respiratory gases. A seal between the outer wall of the tracheal tube and the inner lining of the trachea (the tracheal mucosa) must be formed. Most endotracheal tubes (except those for small children) provide a very compliant, thin walled inflatable cuff that forms a seal with the proximal tracheal rings. This seal allows for positive pressure ventilation at normal airway pressures with minimal leakage. The seal thus provides a closed circuit for ventilation and also prevents aspiration of pharyngeal contents into the respiratory tract. This seal is usually formed by inflating a pressurized cuff that surrounds the tracheal tube. The pressure in the cuff must be adequate to form a seal, but it is known that over-pressurization will cause tracheal trauma including hemorrhage, ulcers, perforation and strictures. The main cause of trauma is the loss of blood flow (ischemia) and resultant necrosis of the tracheal lining.

Cuff pressures are typically set between 10–50 mm Hg. This range of pressures is relatively wide and for any particular patient the formation of a seal without creating an ischemia will require holding the pressure in a much narrower range. Moreover, because tracheal tubes are used in a dynamic environment, the pressure required to maintain an adequate seal will vary. Finally, cuff pressure will vary due to the diffusion of nitrous oxide into the cuff. Thus, establishing a correct cuff pressure and correctly regulating the cuff to this pressure are both important. For example, during mechanical ventilation, the intracuff pressure must be low enough to allow tracheal capillary perfusion, thus reducing the risk of ischemia, while being high enough to prevent either loss of tidal volume or significant aspiration.

The use of high volume, low pressure endotracheal tube cuffs starting in 1973 reduced the incidence of complications from prolonged tracheal intubation. This more compliant cuff design provides a satisfactory tracheal seal for positive pressure ventilation associated with significantly lower cuff-tracheal mucosa contact pressure. Unfortunately, when lung compliance significantly decreases—as often occurs in critically ill ICU patients—high airway pressures are transmitted through the distal cuff surface during inspiration. Cuff-tracheal mucosal contact pressures approach peak airway pressures as high as 50 mm Hg during each inspiration. This contact pressure far exceeds tracheal mucosal perfusion pressure of 15 mm Hg and significant ischemic damage can occur, and in fact mucosal ischemic damage commonly occurs in observed patient populations. Endoscopic and biopsy studies suggest a high incidence of mucosal ulceration, cartilage infiltration with bacteria, and ultimately, scar formation with the development of clinically significant airway narrowing. Local mucosal defense mechanisms are inhibited during tissue ischemia, allowing bacteria to multiple and invade deeper structures.

An additional cause of cuff pressures that exceed mucosal perfusion pressure is brought about during nitrous oxide general anesthesia. Nitrous oxide diffuses into a cuff eighty times faster than nitrogen diffuses outward, producing a significant increase in cuff volume such that cuff pressures often exceed 60 mm Hg, and the above-described ischemia and deterioration of the mucosa result.

Others have recognized and proposed solutions to the problems associated with excessive cuff pressures during prolonged intubation. For example, U.S. Pat. No. 5,235,973—Levinson discloses a system for monitoring and controlling cuff pressure that requires both an inflation line and a monitoring line connected to the cuff. The monitoring line is used to determine when additional pressure should be applied to the cuff, and is governed by the pressure in the inspiration line of the ventilator. However, this system raises cuff pressure with each inspiration to avoid loss of tidal volume without regard for cuff-mucosal perfusion pressure and thus cannot provide satisfactory pressure regulation. Another pressure control system is disclosed in U.S. Pat. No. 4,924,862—Levinson. In this system, pressure relief valves connect the cuff and a source of pressurized gas. A high pressure relief valve regulates cuff over-pressure, while a low pressure relief valve is controlled by a flow detector monitoring the cuff inflation line. A continuous flow in the cuff inflation line is indicative of a cuff leak. Cuff pressure regulation via mechanical valves is disclosed by U.S. Pat. Nos. 4,770,170 and 4,825,862 both to Sato et al. However, as well known to those of skill in the art, mechanical valves have performed poorly in clinical use.

One pressure regulation device known as the Cardiff Cuff Controller has been reported in the literature. See Morris et al., J. Med. Eng. & Tech., Vol. 9, No. 5 (Sept./Oct. 1985) at pp. 229–30; Cobley et al., "Endobronchial Cuff Pressures," *British J. Anesthesia*, 70:576–78 (1993). This device regulates cuff pressure using an air reservoir and pump that connect to the cuff via a controlled valve. A relief valve is also provided to alleviate over-pressure conditions. Use of this device is also reported in the literature. See Willis et al., "Tracheal tube cuff pressure: Clinical use of the Cardiff Cuff Controller," Anethaesthesia 43:312–14 (1988); and Cobley et al., referenced immediately above.

As explained above, the prevalence of tracheal tubes, and in particular endotracheal tubes, has led to detrimental effects being observed, particularly when patients are intubated for a long period of time. For example, pulmonary complications are caused by aspiration during prolonged orotracheal intubation. The current use of high volume, low pressure cuffs alleviates this problem to a certain extent. See Spray et al., "Aspiration Pneumonia: Incidence of Aspiration with Endotracheal Tubes," Am. J. Surg. 131:701–03 (June, 1976). However, aspiration can and does occur even using a properly designed high volume, low pressure cuff inflated to and maintained at an appropriate pressure. Regurgitated gastric fluids and pharyngeal secretions that enter the proximal trachea often accumulate above the inflated cuff and may channel to soil the more distal trachea and lungs.

Physicians believe this pathway to be the most common mechanism producing hospital acquired bronchitis and pneumonia. As many as twenty-five percent (25%) of patients requiring more than several days of intubation and ventilation within an ICU develop nosocomial pneumonia. Typically, oral and pharyngeal secretions are removed by nursing personnel on an as-needed basis. However, the hand-held suction catheters currently in use fail to drain the subglottic region. As much as 150–200 ml of liquid secretions have been removed over a 24 hour period in one study using once hourly manual syringe evacuation. Significant problems with thick, viscous secretions plagued prior endotracheal tubes that attempted to drain this region. Small bore suction tubing has to be replaced with much larger total volume tubing but not at the expense of greatly increasing the outer diameter of the endotracheal tube at the vocal cord level.

The literature reports a relationship between upper gastrointestinal, oropharyngeal colonization and the occurrence of pneumonia. See Mahul et al. "Prevention of nosocomial pneumonia in intubated patients: respective role of mechanical subglottic secretions drainage and stress ulcer prophylaxis," Intensive Care Med. 18:20–25 (1992). In the Mahul et al. study, both hourly drainage of subglottic secretions and the use of sucralfate or antacids as a prophylactic measure were tried as alternative methods of preventing pneumonia. The drainage of subglottic secretions was performed using a HI-LO EVAC endotracheal tube manufactured by Mallinkrodt; this tube has an elliptic dorsal opening above the cuff that is connected to a separate, integral aspiration lumen. A small bore suction channel was incorporated into the wall of the tube with its distal opening 5.0 mm above the inflated cuff. The antacid cytoprotective agent was administered via a nasogastric tube separate and distinct from the endotracheal tube. It is noted that prior study of this type of endotracheal tube by this inventor's laboratory found a high incidence of suction channel blockage with long term use. In addition, the rate and viscosity of removed secretions is greatly limited by the small lumen.

Thus, in a long term intubation subject, pathogenic bacteria multiply in the pool of secretions that accumulate above the inflated endotracheal tube cuff, providing a significant inoculum when aspirated into the distal trachea. Irrigation and drainage are the methods of choice when attempting to remove infected material from the body. Irrigation dilutes the bacterial colony count and suction drainage removes this material from the body. Applying this technique to the area below the vocal cords and above the inflated cuff (subglottic region), may reduce the incidence and amount of infected secretions that reach the lungs and therefore prevent nosocomial pneumonias. Subglottic irrigation with a bactericidal solution may also significantly decrease the infectivity of secretions that may be aspirated into the distal trachea.

For the foregoing reasons, others have attempted to construct endotracheal tubes that incorporate a suction device to draw fluids from the pharynx or a channel to irrigate a body area. U.S. Pat. No. 2,854,982 discloses a nasopharyngeal tube that comprises an outer tube surrounding a central lumen. The outer tube includes orifices for providing suction above the cuff. U.S. Pat. 3,593,713 discloses a device similar to the aforementioned patent but uses the outer tube to provide irrigation. U.S. Pat. No. 4,468,216 also discloses an irrigation/suction catheter with a central lumen surrounded by an outer tube. The outer tube is used to suction liquids provided via the central lumen.

Despite the above-described attempts of the prior art, however, there are currently no fully satisfactory tracheal tubes that can be left in place for long periods of time. As shown above, it is desirable to regulate the cuff pressure of a tracheal tube. Maintaining such a constant, controlled cuff pressure avoids under-inflation, and the concomitant loss of the mechanical barrier against gross spread of secretions. It is also desirable to avoid over-inflation and thus avoid ischemic mucosal damage that inhibits the local host defenses against infection. It is further desirable to prevent the distal spread of infected subglottic secretions. Toward this end, the subglottic region should be drained and it is further desirable to dilute the bacterial inoculum by irrigation and possibly with bactericidal medication and to frequently remove this material by suction, prior to channeling around the inflated cuff. Such steps will reduce the incidence of conditions such as nosocomial pneumonia and irritation of the mucosa.

It is therefore an object of the present invention to provide methods and apparatus for intubating a patient that simultaneously irrigates the subglottic region with saline or a bactericidal solution, frequently drains the subglottic secretions by controlled suction, and by servoregulating cuff pressure over a very narrow range. It is a further object of the present invention to provide such methods and apparatus in a form that is simple and efficient, and that can be easily manufactured.

SUMMARY OF THE INVENTION

It has now been found that the problems discussed above are overcome by providing a coordinated system that improves the mechanical barrier against aspiration. A modified endotracheal tube comprising an airway lumen defined by an outer wall with an inflatable cuff disposed around the outer wall and connected to a cuff pressure line that also includes a subglottic suction lumen having a distal end terminating at an opening proximal of the inflatable cuff, and an irrigation lumen having a distal end terminating at an opening proximal of the inflatable cuff. In preferred embodiments of the present invention either the cuff pressure line, or irrigation lumen may be integral with the outer wall of the tracheal tube. In certain preferred embodiments, one or both of the subglottic suction lumen and the irrigation lumen are concentric with the airway lumen. In other preferred embodiments, the distal ends of the cuff pressure line, the subglottic suction lumen, and the irrigation lumen are all terminated by a connector, such as those familiar to those of skill in the art. The apparatus disclosed herein is most preferably incorporated into endotracheal tubes.

Thus, the present invention discloses a system for intubating a patient that uses a tracheal tube having an airway lumen connected to a source of gas to be administered to the respiratory system of a patient, an inflatable pressure cuff disposed around the outer wall of the airway lumen, and connected to a cuff pressure line that is in turn connected to a source of pressurized fluid and a fluid pressure regulator. The tracheal tube of this embodiment also includes a subglottic suction lumen having a distal end terminating at an opening proximal of the inflatable cuff and a proximal end connected to a vacuum source and an irrigation lumen having a distal end terminating at an opening proximal of the inflatable cuff and a proximal end connected to a source of irrigation fluid. Preferably, the pressure regulator maintains a preselected cuff pressure between 10 and 30 mm Hg, and most preferably about 15–20 mm Hg. In certain embodiments, the fluid pressure regulator comprises a compressor connected to a reservoir that connects to the cuff pressure line and a pneumatic relief valve disposed between the compressor and the reservoir. Additionally, in other embodiments, the subglottic suction lumen is connected to an automatic suction device, which preferably applies suction for a predetermined period of time at predetermined intervals. The irrigation lumen is preferably connected to an automatic perfusion pump, and it is further preferred that the automatic perfusion pump distributes fluid through the irrigation lumen for a predetermined period of time at predetermined intervals.

The present invention also discloses methods of intubating a patient.

Thus, a modified endotracheal tube has been developed that provides a means to deliver an irrigating solution to the subglottic region and a specialized outer sleeve that directs significant suction drainage to the area above the inflated cuff. A standard endotracheal tube having a curved, thick-walled shaft, a proximal connector, and a distal inflatable high-volume, low pressure cuff with associated inflation channel and pilot valve, has been modified to provide an irrigation channel in the concave side of the shaft wall with its proximal end consisting of a leur lock connector and its distal end opening immediately above the inflated cuff. A suction channel has been incorporated around the outside surface of the endotracheal tube shaft consisting of a compliant, thin walled sleeve that tapers from the proximal to the distal end. The sleeve is preferably approximately 8.0 mm wider than the tube shaft in the most proximal location with a gradual taper only 1.0 mm wider at the distal attachment. The sleeve is attached immediately above the inflated cuff, with rounded edges to prevent tissue trauma. The compliant nature of the sleeve provides a large area for suction but molds to the glottic tissues, thereby minimally increasing the outer diameter of the endotracheal tube at the vocal cord level. Laboratory study suggests 0.30 mm PVC plastic to be a satisfactory material for this use. The proximal sleeve is attached to a large bore suction catheter, (preferably greater than 6 French) such that the entire inside circumference of the sleeve easily drains.

The present invention also includes an electromechanical device that regulates and coordinates each function of the modified endotracheal tube. A simple volume regulated infusion pump is used to deliver a controlled amount of non-viscous liquid to the irrigation channel of the endotracheal tube. The infusion may be adjusted from 0 to 30 ml/hr and will be abruptly stopped if cuff pressure or suction pressure are lost. Subglottic suction is regulated by a device that down-regulates wall suction from 300 mm Hg to an adjustable suction of 0–150 mm Hg. A timing device, powered by the force of wall suction, will regulate the on-off cycle. A short period of suction will be followed by several minutes of silence. Suction from this device will be directed through the subglottic suction catheter, down the sleeve, to the area above the inflated cuff.

Finally, it is preferred that cuff pressure is closely regulated by an electronic servomechanism that maintains pressure near a preselected value. This servomechanism quickly adjusts cuff pressure over a wide range of clinical environments such as positive pressure ventilation with high airway pressures, coughing, and during the changing volumes associated with nitrous oxide anesthesia. Unique to the present invention is a very rapid and accurate electronic valve solenoid that can adjust cuff pressure within 0.30 seconds without overshoot. This allows attenuation of elevated cuff pressure that always occurs when high inspiratory airway pressures are transmitted through the underside of the inflated cuff. In certain embodiments, the pressure regulator maintains a preselected pressure in the range of 10–50 mm Hg, and most preferably below mucosal perfusion pressure of 15 mm Hg. This device consists of an air compressor, electronically controlled pneumatic relief valve, and a non-compliant reservoir. Output from this pressure regulator is attached to the pilot valve of the cuff inflation channel.

BRIEF DESCRIPTION OF THE DRAWINGS

FIG. 1 is a partially schematic, partially diagrammatic illustration of the system of the present invention;

FIG. 2 is a cross-section of a preferred embodiment of the distal tracheal tube of the present invention, taken along lines 2—2 in FIG. 1.

FIG. 3 is a cross-section of a preferred embodiment of the proximal tracheal tube of the present invention, taken along lines 3—3 in FIG. 1.

DETAILED DESCRIPTION OF THE PREFERRED EMBODIMENTS

Referring to FIG. 1, there is shown a partially schematic, partially diagrammatic illustration of the system of the present invention. A patient 50, illustrated in cross-section through the median plane, is nasally intubated using a tracheal tube 100 made in accordance with the present invention. The area below the vocal cords 52, and above the inflated cuff 150 is defined as the subglottic region 54.

As seen in FIGS. 1–3, the tracheal tube 100 comprises an airway lumen 108 in a compliant shaft 102 defined by an inner wall 104 and an outer wall 106. As well known to those of skill in the art, this lumen 102 permits fluids to be transferred into and out of the airways of the patient 50. Surrounding the outer wall 104 is an inflatable cuff 106 and a thin-walled, compliant sleeve 110 circumferential with the shaft 102. Most preferably, the proximal end is 8.0 mm wider than the outer shaft wall 106. This sleeve 110 gradually tapers to a width 1.0 mm greater than the outer shaft wall 106. As seen in FIG. 2 at its distal end, the outer sleeve 110 attaches to the outer shaft wall 106 at four equally spaced points 112, i.e., 3, 6, 9, and 12 o'clock. This attachment is located approximately 2.0 mm above the inflated cuff 150. Incorporated into the convex wall of the shaft is the cuff inflation channel 154 terminating into the inner atmosphere of the cuff 150. The inflatable cuff 150 is thus attached by a line 154 to the cuff pressure regulator line 252 via a pilot valve 152.

As also seen in FIG. 1, the cuff pressure line 252 is connected to a cuff pressure regulator system 200 via a pilot valve 152. The servoregulator 200 most preferably includes a compressor 208, connected to a reservoir 206. A pneumatic pressure relief valve 210 disposed between the compressor 208 and the reservoir 206 regulates the pressure in the reservoir 206. The cuff pressure servoregulator 204 also preferably includes a numerical display 202 that permits the user to visually determine the pressure being delivered to the cuff 150. The cuff pressure servoregulator 204 includes feedback circuits and sensors that compare the pressure sensed to the predetermined pressure set by an operator. If the pressure is too low, additional gas is permitted to flow to the cuff 150, either by release from the reservoir 206 or by operating the compressor 208. If the pressure exceeds a predetermined maximum, pressure is relieved by allowing gas to escape from the pneumatic relief valve 210.

Most preferably, the pressure servoregulator 204 comprises an electronic servomechanism that autoregulates cuff pressure in the range of 0–60 mm Hg, although it is preferred that the predetermined pressure be set between 10–30 mm Hg, and most preferably between about 15–20 mm Hg. Cuff-tracheal mucosal contact pressure (approximate to cuff pressure) greater than 15 mm Hg has been shown to significantly decrease tissue perfusion. The present invention most preferably uses equipment that can regulate the predetermined pressure within about ±2.0 mm Hg. Pressure regulation will occur within 0.30 seconds of detecting a change from baseline. This will attenuate cuff pressure increases transmitted during the inspiratory phase of positive pressure ventilation. This fast and accurate servoregulation is unique to the electronic methods described in the present invention. In use, the lowest pressure that provides a seal during positive pressure ventilation should be used. In preferred embodiments, air is added to the cuff 150 by an electronically controlled pneumatic valve 204 disposed between the cuff 106 and the reservoir 206.

One device that can be adapted to regulate pressure in accordance with the present invention is the A.T.S.™ 1500 Tourniquet System manufactured by Aspen Labs, a subsidiary of Zimmer, Dover, Ohio (USA). This device regulates the pressure of tourniquets, but can be readily adapted for use in accordance with the present invention. Those of skill is the art will realize that the Zimmer system or other such systems can be easily programmed in accordance with the parameters set forth above and used in a system such as that described and illustrated herein.

As best illustrated in FIG. 2, the tracheal tube 100 of the present invention also includes an irrigation channel 304 preferably incorporated into the wall of the thick walled, curved flexible shaft 102. The irrigation channel 304 delivers non-viscous liquids to the subglottic region 54. The irrigation channel 304 is connected to a liquid reservoir 302 and volume infusion pump 300. This irrigation is useful to prevent drying of the mucosa or for delivery of bactericidal medication to the region. It is preferred that the irrigation system of the present invention delivers non-viscous liquids to the subglottic regions such as dilute antibiotic solutions that provide a chemical barrier to infection. Alternatively irrigation with local anesthetic solutions that provide a field numbing block of the trachea for patient comfort may be useful. Preferably, the liquid is delivered at a rate of about 0–20 ml/hr. It is also preferred that the delivery of the liquid is integrated with the intermittent suction described above.

As explained above, a thin walled, compliant outer sleeve 110 surrounds the outer wall of the endotracheal tube shaft 102. This outer shaft tapers in a proximal to distal direction forming a suction lumen 42 with a 8.0 mm width near the proximal end and a 1.0 width near its distal end. The tapered and compliant nature of this sleeve at body temperature allows a large suction channel without the need to greatly enlarge the outside diameter of the endotracheal tube at the vocal cord level. Most preferably, the distal end of the subglottic suction lumen 142 terminates at an opening immediately proximal of the inflatable cuff 150. A large bore suction catheter 40 is attached to the proximal end of the subglottic suction channel 42 such that fluids easily drain from the entire circumference of the channel. This suction catheter is connected to a suction canister 402 and suction regulatory device 400 that down-regulates wall suction 406 for delivery to the subglottic region.

Among other advantages, this design permits the suction applied to the subglottic suction lumen 42 to provide suction around the periphery of the annular space between the tracheal lining and the outer wall of the tracheal tube 100. Additionally, an annular orifice such as that shown in FIG. 2 is less likely to be occluded during suction. The suction lumen 42 is integrated into a tubular proximal extension, shown in FIG. 1, that includes a connector 44 that connects the suction lumen 42 to a subglottic suction regulator 400. Preferably, a canister 402 for removing aspirated fluids is provided and the suction regulator 400 is connected to a source of suction 406 through a timer. Typically, wall suction 406 is provided at 300 mm Hg, which is most preferably down regulated to a maximum of 150 mm Hg. The timer permits the application of suction to be intermittent.

The present invention thus also discloses improved methods of intubating a patient. In use, the methods of the present invention require inserting a tracheal tube into the patient and inflating an inflatable pressure cuff to a predetermined pressure while regulating the pressure in the inflatable pressure cuff. During intubation, fluid such as anesthetic gas moves through the tracheal tube and into the patient. As described above, the methods of the present invention also include applying suction to a subglottic secretion suction lumen, and irrigating a region by flowing a liquid through an irrigation lumen. By using such improved methods, extended period of intubation can now be effectively achieved while minimizing any related trauma or other adverse conditions.

Although certain embodiments of the present invention have been disclosed herein and described with particularity, these embodiments are intended to illustrate the function and operation of the present invention and are not intended to act as limitations. Upon review of the foregoing description, those of skill in the art will immediately apprehend useful modifications, adaptations and alternate embodiments that utilize the spirit of the present invention. Accordingly, in order to determine the full scope of the present invention, reference should be made to the appended claims.

What is claimed is:

1. An integrated system providing a mechanical and chemical barrier against the spread of secretions into the distal trachea comprising an endotracheal tube, wherein the endotracheal tube comprises:

a thin walled, compliant outer sheath defining a suction channel concentric with an outer wall of the endotracheal tube for removing infected secretions from a subglottic region below the vocal cords and above an inflated cuff, the outer sheath terminating immediately above the inflated endotracheal tube cuff to create a substantially annular suction lumen; and an irrigation channel integral with the outer wall and separate from the annular suction lumen for delivering a non-viscous liquid to the subglottic region for tissue hydration and the dilution of bacterial inoculum, whereby delivery of antibiotic and antifungal medication to the subglottic region provides a chemical barrier against the distal spread of infected secretions, the irrigation channel further providing infusion of topical local anesthetics that are subsequently drained, whereby the local anesthetics produce a numbing field block for awake intubated patients, the system further comprising an electronic and mechanical control device for regulating and integrating irrigation, suction, and cuff pressure, wherein subglottic irrigation will cease if suction or cuff pressure regulation malfunction and wherein an alarm condition is indicated if any one of irrigation, suction and cuff pressure regulation are not functional, wherein cuff pressure is regulated by a cuff pressure autoregulator comprising: an air compressor; a gas reservoir; a pneumatic control valve; an electronic pressure transducer and servoregulator; a digital display; and an electronic alarm system, wherein the air compressor provides cuff pressure control within about 0.30 seconds of a change in pressure to a pressure within 2.0 mm Hg of a desired pressure in the range of 0–60 mm Hg, with a default pressure of about 15 mm Hg, whereby compressed gas from the compressor travels through a cuff pressure control line to connect with a cuff inflation channel in the endotracheal tube.

2. The system of claim 1, wherein the suction channel is connected to wall suction that is down-regulated to an adjustable pressure of about 150 mm Hg and further comprises a mechanical timer for timing control of suction activation and quiescence, whereby suction is activated for a period of about 15–60 seconds followed by a several minute period of quiescence; and further connect a suction canister.

3. The system of claim 1, wherein electronics integrate the function of the system such that liquid infusion is halted if cuff pressure or suction pressure are lost, and wherein electronic alarms provide assurance to the proper function of the system.

* * * * *